United States Patent [19]

Green et al.

[11] Patent Number: 4,948,819

[45] Date of Patent: Aug. 14, 1990

[54] BENZOPHENONE QUATERNARY AMMONIUM LINKED (METH)ACRYLATES, PHOTOCURABLE AND PHOTOCURED PRODUCTS, AND METHOD OF COATING

[75] Inventors: Peter N. Green; William A. Green, both of Liverpool, England

[73] Assignee: Ward Blenkinsop & Company Limited, Cheshire, United Kingdom

[21] Appl. No.: 315,599

[22] Filed: Feb. 27, 1989

[30] Foreign Application Priority Data

Mar. 18, 1988 [GB] United Kingdom ............... 8806527

[51] Int. Cl.$^5$ .................. C07C 69/54; C08F 20/36; C08F 220/36; C08F 2/50
[52] U.S. Cl. .................................. 522/31; 526/288; 526/313; 526/292.2; 427/54.1; 522/34; 522/84; 522/173; 522/905; 560/221
[58] Field of Search ............... 560/221; 526/288, 313, 526/292.2; 522/31, 34, 84, 905; 427/54.1

[56] References Cited

U.S. PATENT DOCUMENTS

| | | | |
|---|---|---|---|
| 4,011,259 | 3/1977 | Samour et al. | 560/221 |
| 4,177,122 | 12/1979 | Sato | 560/221 |
| 4,257,859 | 3/1981 | Fischer | 522/31 |
| 4,310,687 | 1/1982 | Barabas | 560/221 |
| 4,859,727 | 8/1989 | Sasaki | 526/292.2 |

Primary Examiner—John C. Bleutge
Assistant Examiner—Arthur H. Koeckert

[57] ABSTRACT

A compound of general formula

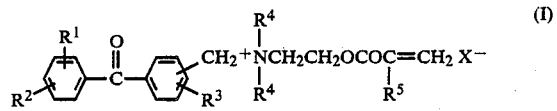

in which $X^-$ represents one equivalent of an anion; $R^5$ represents a hydrogen atom or a methyl group; each $R^4$ independently represents a methyl or ethyl group; and each of $R^1$, $R^2$ and $R^3$ independently represents a hydrogen or halogen atom, an alkyl, alkoxy or alkylthio group having from 1 to 4 carbon atoms, an arylthio group or a group of formula

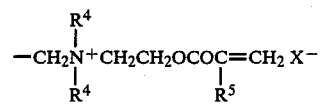

in which $R^4$, $R^5$ and X have the meanings given above, are useful as water soluble co-polymerizable photoinitiators.

9 Claims, No Drawings

BENZOPHENONE QUATERNARY AMMONIUM LINKED (METH)ACRYLATES, PHOTOCURABLE AND PHOTOCURED PRODUCTS, AND METHOD OF COATING

This invention relates to benzophenone derivatives, and their use as photoinitiators, in particular in the preparation of u.v.-cured lacquers.

A wide range of substrates, including metal, wood, paper, board and plastics materials are commonly coated with u.v.-cured lacquer films. Well known examples of coated articles include glossy magazines, books, food wrappers and drinks cans. The lacquers are generally formed by coating the substrates with a polymerisable composition containing a photoinitiator, and then curing the applied composition by exposing it to ultra violet light.

Compositions for the production of u.v.-cured lacquers normally contain a mixture of a lipid soluble prepolymer, a lipid soluble monomer and a lipid soluble photoinitiator. A co-initiator such as N-methyl diethanolamine is sometimes also present. Details of such compositions are given in "U.V. and E.B. curing formulations for printing inks, coatings and paint" edited by R. Holman and published in 1986 by SITA-Technology, U.K. Whilst such formulations can produce excellent u.v.-cured films on a variety of substrates, the monomers employed are often skin irritants, and sometimes it is difficult to achieve the desired composition viscosity without the aid of organic solvents. These problems can be overcome if an aqueous composition is employed, but the number of photoinitiators known to be suitable for use in such compositions is very small.

To be suitable for use in an aqueous composition for the production of u.v.-cured lacquers, a photoinitiator must be highly water soluble over a wide pH range, fast acting, colourless and, preferably, odourless.

When U.V. cured coatings prepared using known water soluble photoinitiators are left in contact with water for any length of time considerable amounts of photoinitiator are released into the water. This phenomenon is highly undesirable if the coatings are, for example, in contact with foodstuffs.

In a paper presented at Rad-Cure 1986 by W. Baeumer, M. Koehler and J. Ohngemach, held at Baltimore, USA, Sept. 8–11th, 1986, there were disclosed certain novel lipid-soluble copolymerisable photoinitiators and their use in the preparation of u.v.-cured lacquers. It is shown that the amount of unreacted photoinitiator, which may be extracted from the u.v.-cured coatings using the organic solvent, acetonitrile, is extremely small if these copolymerisable photoinitiators are used. The paper makes no reference to water soluble photoinitiators.

We have now found certain benzophenone derivatives which are highly suitable as water soluble photoinitiators for the preparation of U.V. cured coatings, and which are released into water from such coatings in only small amounts.

The present invention provides a compound of general formula:

$$\text{R}^1\text{-C}_6\text{H}_3(\text{R}^2)\text{-CO-C}_6\text{H}_3(\text{R}^3)\text{-CH}_2\text{-}^+\text{N}(\text{R}^4)_2\text{CH}_2\text{CH}_2\text{OCOC}(\text{R}^5)=\text{CH}_2 \ \text{X}^- \quad (I)$$

in which X⁻ represents one equivalent of an anion; $R^5$ represents a hydrogen atom or a methyl group; each $R^4$ independently represents a methyl or ethyl group; and each of $R^1$, $R^2$ and $R^3$ independently represents a hydrogen or halogen atom, an alkyl, alkoxy or alkylthio group having from 1 to 4 carbon atoms, an arylthio group, or a group of formula $$-\text{CH}_2\text{N}^+(\text{R}^4)_2\text{CH}_2\text{CH}_2\text{OCOC}(\text{R}^5)=\text{CH}_2\text{X}^-$$

in which $R^4$, $R^5$ and X⁻ have the meanings given above.

An arylthio group may be, for example a p-toluylthio group.

Preferably each of $R^1$, $R^2$ and $R^3$ independently represents a hydrogen atom, a halogen atom, an alkyl or alkoxy group having from 1 to 4 carbon atoms, or a group of formula $$-\text{CH}_2\text{N}^+(\text{R}^4)_2\text{CH}_2\text{CH}_2\text{OCOC}(\text{R}^5)=\text{CH}_2\text{X}^-$$

More preferably $R^2$ and $R^3$ both represent hydrogen atoms, and $R^1$ represents a hydrogen atom, a halogen atom, an alkyl or alkoxy group having from 1 to 4 carbon atoms, or a group of formula $$-\text{CH}_2\text{N}^+(\text{R}^4)_2\text{CH}_2\text{CH}_2\text{OCOC}(\text{R}^5)=\text{CH}_2\text{X}^-$$

Most preferably, $R^2$ and $R^3$ represent hydrogen atoms, and $R^1$ represents a hydrogen atom, a chlorine atom, a methoxy group or a tertiary butyl group.

Each $R^4$ preferably represents a methyl group.

$R^5$ preferably represents a hydrogen atom.

X⁻ preferably represents a halide ion, for example a chloride, or more preferably a bromide ion.

It will be appreciated that in the compounds of formula I, the group $$-\text{CH}_2-\text{N}^+(\text{R}^4)_2-\text{CH}_2\text{CH}_2\text{OCOC}(\text{R}^5)=\text{CH}_2$$

may be in the ortho, meta or para position relative to the benzoyl group. Preferably the group is in the para position.

The group $R^1$ is preferably in the para position relative to the benzoyl carbonyl group.

The invention further provides a process for the preparation of a compound of the general formula I, which comprises reacting a compound of general formula.

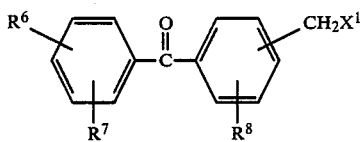

in which each of $R^6$, $R^7$ and $R^8$ independently represents a hydrogen atom, a halogen atom, an alkyl, alkoxy or alkylthio group having from 1 to 4 carbon atoms, an arylthio group, or a group $CH_2X^1$, and $X^1$ represents a leaving atom or group, with a compound of general formula.

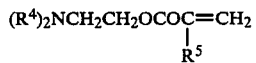

in which $R^4$ and $R^5$ are as earlier defined.

A leaving atom or group represented by $X^1$ may be, for example, a halogen atom (e.g. chlorine or bromine) or a hydrocarbylsulphonyloxy group (e.g. methanesulphonyloxy or p-toluenesulphonyloxy).

The reaction is conveniently carried out in the presence of a suitable solvent, for example a ketone such as acetone or methyl ethyl ketone, or an ester such as ethyl acetate. The reaction temperature is conveniently in the range of from 20° to 100° C., preferably 40° to 60° C., reflux temperature often being convenient.

The compounds of general formula II may be prepared in a facile way by known methods from readily available starting materials. The compounds of general formula III are readily available.

Further in accordance with this invention there is provided an aqueous photocurable composition comprising an aqueous solution of at least one polymerisable prepolymer and, as a photoinitiator, a compound of formula I. Conveniently the compositions will comprise from 0.5 to 10% by weight of photoinitiator. The invention also extends to the use of such a composition for the production of photocured lacquer films, and to substrates coated with such films.

Accordingly, the invention provides a method of producing a substrate coated with a u.v.-cured lacquer film, which comprises applying a composition as described hereinabove to a surface of a substrate and exposing it to ultra violet light.

It is a particular advantage of the compounds of the present invention that they can be used to prepare U.V. cured coatings which release only small quantities of the compound when in contact with water. Further advantage of compounds of the invention are that they are water soluble, colourless and produce odourless U.V. cured coatings.

Suitable photopolymerisable prepolymers include acrylated polyurethanes, polyesters and epoxides, for example those manufactured by Lankro Chemicals Limited, Eccles, U.K., and their water thinnable acrylated polyurethane prepolymer RCP 2702 (Trade Mark) is strongly recommended.

A photopolymerisable composition according to the invention may also if desired contain a water soluble coinitiator. Particularly suitable coinitiators are water soluble tertiary amines, for example triethanolamine, N,N-dimethyl-ethanolamine or N-methyl-diethanolamine. Such co-initiators may conveniently be present in a concentration of from 0 5 to 10% by weight of the total formulation.

The following Examples illustrate the invention.

EXAMPLE 1

4-Benzoyl-N,N-dimethyl-N-(2-(1-oxo-2-propenyloxy)ethyl)benzenemethanaminium bromide Dimethylaminoethyl acrylate (9.11 mls) was added to a stirred solution of 4-bromomethylbenzophenone (13.75g) in acetone (50 mls) at 55° C. and the mixture was stirred for two hours at 60°±2° C. After cooling to room temperature, the stirred mixture was further cooled in an ice bath for two hours prior to filtration. After washing the residue with acetone (X1) followed by isopropyl ether (X2) the solid was dried under vacuo at room temperature. The crude title compound was obtained as a white crystalline solid (14.48g; m.p. 121°–123° C.) which was recrystallised from acetone (150 mls). Filtration, followed by sequentially washing with acetone (X1) then isopropyl ether (X1) and drying under vacuo at room temperature gave the title compound (10.26g; yield =49.04%) as white fine granular crystals of melting point equal to 122°–124° C. Analysis:

Calcd. for $C_{21}H_{24}N\ Br\ O_3$: C 60.29; H 5.78; N 3.35; Br 19.10

Found: C 60.32; H 5.77; N 3.33; Br 19.12

An aqueous solution of this compound has an absorption maximum at 258 nm with an extinction coefficient (1%, 1 cm) of 461.8.

EXAMPLE 2

4-Benzoyl-N,N-dimethyl-N-(2-(2-methyl-1-oxo-2-propenyloxy)ethyl)benzenemethanaminium chloride Dimethylaminoethyl methacrylate (10.13 mls) was added to a stirred solution of 4-chloromethylbenzophenone (11.52g) in acetone (50 mls) at 48° C. and the mixture was stirred for fifteen hours at 48°±2° C. The stirred mixture was cooled in an ice bath for two hours prior to filtration, washing with acetone (X2) and drying under vacuo at room temperature. The crude title compound was obtained as a white crystalline solid (16.82g; m.p. 163°–166° C.) which was recrystallised from a mixture of acetone (30 mls) and isopropanol (30 mls).

Filtration, followed by washing ((50/50//acetone/isopropanol)X2; then acetone X1) and drying in vacuo at room temperature gave the title compound (16.50g; yield=85%) as white crystals of melting point equal to 167.5°–168.5° C.

Analysis:
Calcd. for $C_{22}H_{26}N\ Cl\ O_3$
C 68.12; H 6.75; N 3.61; Cl 9.14
Found: C 68.12; H 6.75; N 3.65; Cl 9.20

An aqueous solution of this compound has an absorption maximum at 260 nm with an extinction coefficient (1%, 1 cm) of 462.

EXAMPLE 3

3-Benzoyl-N,N-dimethyl-N-(2-(1-oxo-2-propenyloxy)ethyl)benzenemethanaminium bromide Dimethylaminoethyl acrylate (11.4 mls) was added to a stirred solution of 3-bromomethylbenzophenone (20.6g) in ethyl acetate (100 mls) at 60° C. and the mixture stirred for 1 hour at 60° C. After cooling to room temperature the mixture was stirred for 1 hour prior to filtration. After washing the residue with ethyl acetate (3x) the solid was dried under vacuo at room temperature. The crude title compound was obtained as a cream solid (27.3g, MP 165°–168° C.) which was recrystallised from propan-2-ol/isopropyl ether. Filtration followed by washing with isopropyl ether then drying under vacuo at room temperature gave the title compound as pale cream crystals. (20.2g, yield =64.5%, MP 168°–169° C.).

Analysis: Calcd. for $C_{21}H_{24}N\ Br\ O_3$
C 60.29; H 5.78; N 3.35; Br 19.10
Found C 60.21; H 5.80; N 3.34; Br 19.16

An aqueous solution of this compound has an absorption maximum at 251 nm with an extinction coefficient (1%, 1cm) of 419.

EXAMPLE 4

4-(4-chlorobenzoyl)-N,N-dimethyl-N-(2-(1-oxo-2propenyloxy)ethyl)benzene methanaminium bromide Dimethylaminoethyl acrylate (7.6 mls) was added to a stirred solution of 4-bromomethyl-4'-chlorobenzophenone in 60 mls ethyl acetate at 60° C. and the mixture stirred at 60° C. for 1 hour. After cooling to room temperature the mixture was stirred for 1 hour prior to filtration. The residue was washed with ethyl acetate (3x) then dried under vacuo at room temperature. The crude title compound was obtained as a white solid (13.7g, MP 143°–145° C.) which was recrystallised from propan-2-ol/isopropyl ether, then drying under vacuo at room temperature gave the title compound as white crystals (13.0g, yield=57.5%, MP 143°–145° C.).

Anaylsis: Calcd. for $C_{21}H_{23}BrClNO_3$
C 55.70; H 5.12; N 3.09; Br 17.65; Cl 7.83
Found C 55.71; H 5.11; N 3.06; Br 17.71; Cl 7.78

An aqueous solution of this compound has an absorption maximum at 257 nm with an extinction coefficient (1%, 1cm) of 421.

EXAMPLE 5

4-(4-methoxybenzoyl)-N,N-dimethyl-N-(2-(1-oxo-2-propenyloxy)ethyl)benzene methanaminium bromide Dimethylaminoethyl acrylate (7.6 mls) was added to a stirred solution of 4-bromomethyl-4'methoxybenzophenone in ethyl acetate (50 mls) at 60° C. and stirred at 60° C. for 1 hour. After cooling to room temperature the mixture was stirred for 1 hour prior to filtration. The residue was washed with ethyl acetate (3x) then dried under vacuo at room temperature. The crude title compound was obtained as white crystals (16.6g, MP 168° –170° C.) which were recrystallised from ethanol/isopropylether. Filtration followed by washing with isopropyl ether then drying under vacuo at room temperature gave the title compound as white crystals (15.7g, yield=70.1%, MP 168° –169° C.).

Analysis: Calcd. for $C_{22}H_{26}BrNO_4$
C 58.93; H 5.85; N 3.12; Br 17.82
Found C 58.97; H 5.90; N 3.09; Br 17.92

An aqueous solution of this compound has an absorption maximum at 298 nm with an extinction coefficient (1%, 1 cm) of 357.

EXAMPLE 6

4-(4-tert. butylbenzoyl)-N,N-dimethyl-N-(2-(1-oxo-2-propenyloxy)ethyl)benzenemethanaminium bromide Dimethylaminoethyl acrylate (7.6 mls) was added to a stirred solution of 4-bromomethyl-4'-tert. butylbenzophenone in ethyl acetate (50 mls) at 60° C. and stirred at 60° C. for 1 hour. After cooling to room temperature the mixture was stirred for 1 hour and an oil separated. The solvent layer was decanted off and the oil dissolved in ethanol (6 mls) at 60° C. then isopropyl ether (15 mls) was added and the mixture cooled to room temperature. Solid crystals separated and were filtered off, washed with ethanol/isopropyl ether (2x) and dried in vacuo at room temperature. The crude title compound was obtained as creamy crystals (4.1g, MP 148°–150° C.) which was recrystallised twice from propan-2-ol/isopropyl ether. Filtration followed by washing with isopropyl ether then drying under vacuo at room temperature gave the title compound as pale cream crystals (0.6g, yield=2.5%, MP 153°–155° C.).

Analysis: Calcd. for $C_{25}H_{32}Br\ NO_3\ 0.5\ H_2O$
C 62.11; H 6.88; N 2.91
Found C 61.84; H 6.80; N 2.93

An aqueous solution of this compound has an absorption maximum at 258 nm with an extinction coefficient (1%, 1cm) of 329.

EXAMPLE 7

Comparison of the efficiency of the Compounds of Examples 1 to 6 with a known photoinitiator Photocurable compositions were prepared by mixing Lankro's prepolymer RCP 2702 (Trade Mark) (3.1 g), water (1.75 mls) and a photoinitiator (0.00043 mole) until homogeneous liquids were obtained. These compositions were coated onto glass microscope slides using a No. 2 Bar coater and the resultant slides were exposed to U.V. light in a single lamp "Minicure" (Trade Mark) apparatus using a conveyor belt speed of 20 r.p.m. for the minimum number of passes required to produce the maximum pencil hardness of the cured film namely 3H. The cured films were then scraped off using a scalpel and the shavings from ten such slides were combined. 0.26 Gram of the latter was transferred to a 70 ml Soxhlet thimble and covered with a layer of glass wool. Distilled water (130 mls) was poured into the Soxhlet apparatus which caused syphonation to occur and approx. 90 mls of water collected in the reservoir of which 85 mls was transferred to a measuring cylinder and 40 mls of this was immediately poured into the Soxhlet thimble. After standing for seven minutes at room temperature the remaining 45 mls was added and syphonation soon occurred. This cycle was repeated ten times—total time for each cycle was found to be ten minutes. Therefore the U.V. cured shavings were extracted ten times with ten minutes immersion per cycle. At this point, the water in the reservoir was analysed for its photoinitiator content by H.P.L.C. whilst the U.V. cured shavings were rapidly washed with distilled water (90 mls, 3 times) before being subject to a second ten cycle extraction and wash routine initially using 90 mls of distilled water. At the end of this process the reservoir water was analysed for the photoinitiator content of the second extract.

The results are given in the table below:

| Photoinitiator | Min. No. of passes to give 3H hardness | % Extracted Photoinitiator content | | Appearance of film |
|---|---|---|---|---|
| | | 1st extract | 2nd extract | |
| *Known photoinitiator | 22 | 51.6 | 3.3 | High gloss, amine like odor |
| Example 1 | 30 | 1.5 | <1.5 | High gloss, odorless |
| Example 2 | 30 | 1.4 | 1.4 | High gloss, odorless |
| Example 3 | 34 | 2.7 | <0.2 | High gloss, odorless |
| Example 4 | 26 | 8.2 | <0.2 | High gloss, odorless |
| Example 5 | 26 | 2.0 | <0.2 | High gloss, odorless |
| Example 6 | 26 | <1.5 | <1.5 | High gloss, odorless |

The results clearly demonstrate the superiority of the compounds of the invention over the known photoinitiator. The known photoinitiator is 4-benzoyl-N,N,N-trimethylbenzenemethanaminium chloride, and is commercially available.

We claim:

1. A compound of general formula

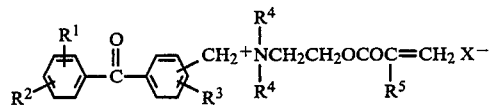

(I)

in which $X^-$ represents one equivalent of an anion; $R^5$ represents a hydrogen atom or a methyl group; each $R^4$ independently represents a methyl or ethyl group; and each of $R^1$, $R^2$ and $R^3$ independently represents a hydrogen or halogen atom, an alkyl, alkoxy or alkylthio group having from 1 to 4 carbon atoms, an arylthio group, or a group of formula

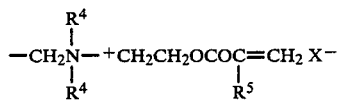

in which $R^4$, $R^5$ and $X^-$ have the meanings given above.

2. A compound as claimed in claim 1, in which each of $R^1$, $R^2$ and $R^3$ independently represents a hydrogen atom, a halogen atom, an alkyl or alkoxy group having from 1 to 4 carbon atoms, or a group of formula

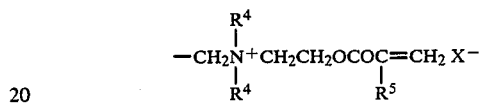

in which $R^4$, $R^5$ and $X^-$ have the meanings given in claim 1.

3. A compound as claimed in claim 2, in which $R^2$ and $R^3$ both represent hydrogen atoms, and $R^1$ represents a hydrogen atom, a halogen atom, an alkyl or alkoxy group having from 1 to 4 carbon atoms, or a group of formula

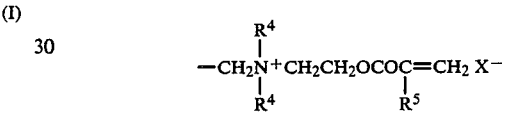

4. A compound as claimed in claim 3, in which $R^1$ represents a hydrogen atom, a chlorine atom, a methoxy group or a tertiary butyl group.

5. A compound as claimed in any one of claims 1 to 4, in which each $R^4$ represents a methyl group.

6. A compound as claimed in any one of claims 1 to 4, in which $X^-$ represents a halide ion.

7. An aqueous photopolymerisable composition comprising an aqueous solution of at least one polymerisable prepolymer and, as photoinitiator, a compound as claimed in claim 1.

8. A method of producing a substrate coated with a u.v.-cured lacquer film, which comprises applying a composition according to claim 7 to a surface of a substrate and exposing it to ultra violet light.

9. A substrate coated with a u.v.-cured lacquer film, when prepared according to the method of claim 8.

* * * * *